United States Patent
Kelly et al.

(10) Patent No.: US 11,491,306 B2
(45) Date of Patent: Nov. 8, 2022

(54) BI-LATERAL CATHETER SYSTEM AND METHODS FOR USE

(71) Applicant: SANFORD HEALTH, Sioux Falls, SD (US)

(72) Inventors: Patrick W. Kelly, Sioux Falls, SD (US); Joel M. Wasdyke, Minneapolis, MN (US); Roger W. McGowan, Minneapolis, MN (US); Patrick A. Haverkost, Minneapolis, MN (US); Alex James Wiedmann, Minneapolis, MN (US)

(73) Assignee: Sanford Health, Sioux Falls, SD (US)

( * ) Notice: Subject to any disclaimer, the term of this patent is extended or adjusted under 35 U.S.C. 154(b) by 209 days.

(21) Appl. No.: 16/652,855

(22) PCT Filed: Oct. 3, 2018

(86) PCT No.: PCT/US2018/054128
§ 371 (c)(1),
(2) Date: Apr. 1, 2020

(87) PCT Pub. No.: WO2019/070828
PCT Pub. Date: Apr. 11, 2019

(65) Prior Publication Data
US 2020/0230351 A1      Jul. 23, 2020

Related U.S. Application Data

(60) Provisional application No. 62/567,264, filed on Oct. 3, 2017.

(51) Int. Cl.
*A61M 25/00* (2006.01)
*A61M 5/142* (2006.01)
(Continued)

(52) U.S. Cl.
CPC ...... *A61M 25/003* (2013.01); *A61M 5/14276* (2013.01); *A61M 25/007* (2013.01);
(Continued)

(58) Field of Classification Search
CPC ............ A61M 5/14276; A61M 25/003; A61M 25/0068; A61M 25/007; A61M 25/0075;
(Continued)

(56) References Cited

U.S. PATENT DOCUMENTS 5,637,086 A * 6/1997 Ferguson ............... A61M 25/10
                                                    604/509
5,718,692 A * 2/1998 Schon ................. A61M 25/007
                                                    604/264

(Continued)

FOREIGN PATENT DOCUMENTS

EP           3108829           7/2013

OTHER PUBLICATIONS

The International Search Report (ISR) with Written Opinion for PCT/US2018/054128 dated Jan. 30, 2019, pp. 1-19.

*Primary Examiner* — James D Ponton
(74) *Attorney, Agent, or Firm* — McDonnell Boehnen Hulbert & Berghoff LLP

(57) ABSTRACT

The present disclosure provides an apparatus including a first tubular housing including a first exit port and a second tubular housing including a second exit port. The apparatus also includes a third tubular housing coupled to at least one of the first tubular housing and the second tubular housing such that each of the first tubular housing, the second tubular housing, and the third tubular housing are fixed with respect to one another. The apparatus also includes a first catheter including a first plurality of outlets and is configured to be positioned at least partially within the first tubular housing. The apparatus also includes a second catheter including a (Continued)

second plurality of outlets and is configured to be positioned at least partially within of the second tubular housing. The apparatus also includes a pressure transducer line positioned in the third tubular housing and a pressure transducer coupled to the pressure transducer line.

31 Claims, 11 Drawing Sheets

(51) Int. Cl.
  *A61M 25/04* (2006.01)
  *A61M 25/10* (2013.01)
(52) U.S. Cl.
  CPC .... *A61M 25/0068* (2013.01); *A61M 25/0075* (2013.01); *A61M 25/04* (2013.01); *A61M 25/10* (2013.01); *A61M 2025/0002* (2013.01); *A61M 2025/0004* (2013.01); *A61M 2025/0034* (2013.01); *A61M 2025/0037* (2013.01); *A61M 2230/06* (2013.01); *A61M 2230/205* (2013.01); *A61M 2230/30* (2013.01)
(58) Field of Classification Search
  CPC ............... A61M 25/04; A61M 25/10; A61M 2025/0002; A61M 2025/0037; A61M 2025/0039; A61M 2025/004; A61M 2230/06; A61M 2230/205; A61M 2230/30
  See application file for complete search history.

(56) References Cited

U.S. PATENT DOCUMENTS

| | | | |
|---|---|---|---|
| 6,565,552 B1 | 5/2003 | Barbut | |
| 2002/0138031 A1* | 9/2002 | Ross | A61M 1/3653 604/4.01 |
| 2004/0030281 A1* | 2/2004 | Goble | A61P 23/00 604/28 |
| 2005/0245882 A1* | 11/2005 | Elkins | A61M 25/0068 604/239 |
| 2005/0283179 A1* | 12/2005 | Lentz | A61M 25/0662 606/192 |
| 2006/0036218 A1* | 2/2006 | Goodson | A61M 29/02 604/264 |
| 2008/0051714 A1* | 2/2008 | Moberg | A61M 5/14248 604/135 |
| 2010/0234698 A1* | 9/2010 | Manstrom | A61B 5/0261 600/301 |
| 2011/0092955 A1 | 4/2011 | Purdy et al. | |
| 2013/0281761 A1 | 10/2013 | Kapur | |
| 2015/0245863 A1* | 9/2015 | Fischell | A61B 18/00 600/424 |
| 2016/0303321 A1 | 10/2016 | Kelly | |
| 2017/0165457 A1* | 6/2017 | Zhadkevich | A61B 5/02158 |

* cited by examiner

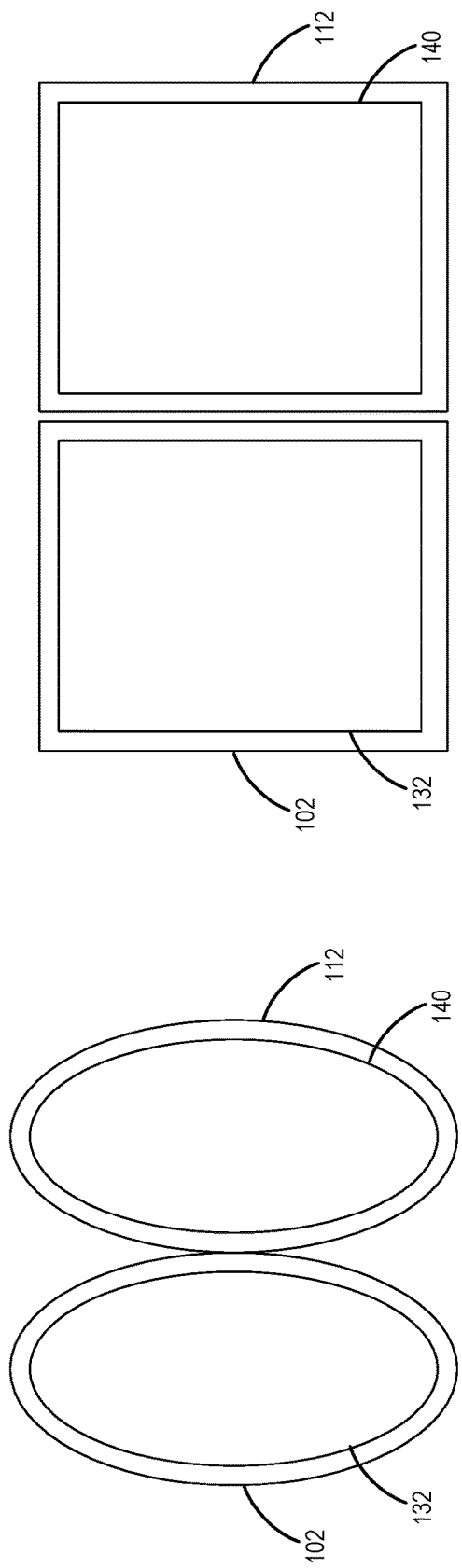
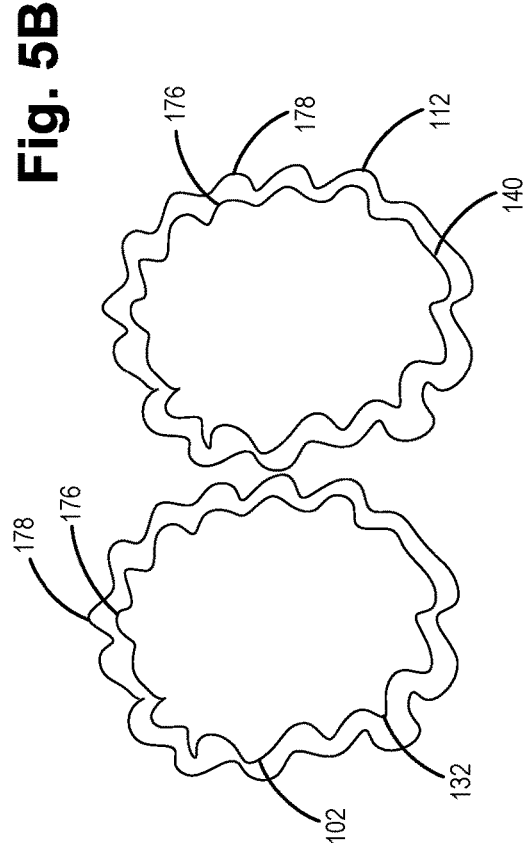

BI-LATERAL CATHETER SYSTEM AND METHODS FOR USE

RELATED APPLICATIONS

This application is a U.S. national phase of International Application No. PCT/US2018/054128, filed on Oct. 3, 2018, which claims priority to U.S. Provisional Application No. 62/567,264, filed Oct. 3, 2017, both of which are incorporated by reference herein in their entirety.

BACKGROUND THE INVENTION

Pulmonary embolism is a blockage of the main artery (i.e., saddle emboli) of the lung or multiple bilateral branches by a substance that has travelled from elsewhere in the body through the bloodstream. The resulting obstruction of the blood flow through the lungs may cause increased pressure on the right ventricle of the heart that may lead to one or more of the following: dyspnea (i.e., shortness of breath), tachypnea (i.e., rapid breathing), chest pain of a "pleuritic" nature that is worsened by breathing, and/or cough and hemoptysis (i.e., coughing up blood). The occurrence of this condition is about 1-2 per 1000 people per capita in the United States, and the likelihood of having a pulmonary embolism increases with age. After 80 years of age, a pulmonary embolism carries a 30% thirty day mortality using current standard of care of anticoagulation. Anticoagulant therapy is a common treatment for pulmonary embolisms. However, delivery of the treatment solution to the location in the pulmonary artery where the embolism is located may be clumsy and less than ideal. For example, current treatment methods include creating multiple holes in a unilateral femoral vein or multiple holes in bilateral femoral veins in order to obtain access to place multiple catheters in the right and left pulmonary arteries. Such methods may increase the risk of bleeding during and after treatment. Multiple access sites in a single femoral vein can increase the risk of hematoma. Further, when the systemic or catheter-directed anticoagulant is being actively administered in vivo, there is no way to know when the blockage has been completely removed thereby needlessly prolonging treatment in some cases. This extended treatment may further result in exposure of a patient to the lytic thereby increasing their risk of a devastating bleeding complication, such as cerebral hemorrhage.

Pulmonary hypertension is a type of high blood pressure that affects the arteries in the lungs and the right side of the heart. Pulmonary hypertension begins when pulmonary arteries and capillaries become narrowed, blocked, or destroyed. This makes it harder for blood to flow through the lungs, and raises pressure within the lungs' arteries. As the pressure builds, the right ventricle of the heart must work harder to pump blood through the lungs, eventually leading to right-side heart failure and hypoxia. Pulmonary hypertension is a serious illness that becomes progressively worse and is sometimes fatal. Signs and symptoms include shortness of breath, fatigue, dizziness or fainting, chest pressure or pain, swelling in the ankles, bluish color in the lips, and racing pulse or heart palpitations.

Right heart catheterization may be helpful for diagnosing pulmonary hypertension. During such a procedure, a catheter is placed into a vein in the patient's neck or groin. The catheter is then threaded into the patient's right ventricle and pulmonary artery. Right heart catheterization allows a medical professional to directly measure the pressure in the main pulmonary arteries and right ventricle. Such a procedure may also be used to monitor the effect medication may have on pulmonary hypertension of the patient. With a pressure sensing line in the pulmonary arteries, if the operator injects a drug and notes a decrease in pulmonary artery pressures, the medical professional may determine that that drug may be a good option for the particular patient.

There are a few medications that can be used to treat pulmonary hypertension with varying degrees of efficacy. Blood vessel dilators (vasodilators) open narrowed blood vessels. One of the most commonly prescribed vasodilators for pulmonary hypertension is epoprostenol (Flolan). A drawback is that the effect may only last a few minutes. This drug is continuously injected through an intravenous catheter via a small pump worn on the belt or shoulder. The patient may have to mix their own medications and may require frequent follow-up from a medical professional. A related drug, iloprost (Ventavis) can be inhaled every three hours through a nebulizer, a machine that vaporizes the medication. Inhalation of the drug may permit the drug to be delivered directly to the lungs. An alternative drug may include endothelin receptor antagonists that may reverse the effects of endothelin, a substance in the walls of blood vessels that causes them to narrow. Another medication that may stop the narrowing of blood vessels is Ambrisentan (Letairis). Sildenafil (Viagra) and tadalafil (Cialis) may be used and work to open the blood vessels in the lungs. In addition, high-dose calcium channel blockers are drugs that may help relax the muscles in the walls of blood vessels. They include medications such as amlodipine (Norvasc), diltiazem (Cardizem, Tiazac), and nifedipine (Adalat, Procardia). Only a small number of patients suffering from pulmonary hypertension respond to calcium channel blockers. Diuretics can also be used. They are commonly known as water pills, and help eliminate excess fluid from the body. This may reduce the amount of work an individual's heart has to perform and may also help limit fluid buildup in the lungs.

Surgical options are limited for patients suffering from pulmonary hypertension. Atrial septostomy is an open-heart surgery that may be an option, but only for patients who do not respond to medication. In an atrial septostomy, a surgeon may create an opening between the left and right chambers of the heart to relieve pressure on the right side of the heart. Atrial septostomy may have serious complications including heart rhythm abnormalities (arrhythmias). Transplantation is another option in some cases for younger patients with idiopathic pulmonary hypertension. However, transplantation carries significant risks including rejection of the transplanted organ and serious infection, and the patient must take immunosuppressant drugs for the rest of their life to help reduce the chance of rejection.

Heart failure may occur when abnormal cardiac function causes failure of the heart to pump blood at a rate sufficient for metabolic requirements under normal filling pressure. Heart failure may be characterized clinically by breathlessness, effort intolerance, fluid retention, and poor survival. Heart failure may be caused by systolic or diastolic dysfunction. For example, left ventricular systolic dysfunction may be defined as left ventricular ejection fraction<0.40. Diastolic heart failure may be defined as a condition in which the heart does not fill with blood properly, and may be difficult to diagnose. Directly monitoring pulmonary artery pressure via a procedure called right-heart catheterization is standard-of-care for hospitalized heart failure patients. However, in view of the chronic nature of heart failure, the patient may spend many days outside of the hospital, making at-home monitoring important. Systems have been developed for micro-electromechanical monitoring of pulmonary artery pressure as a means for early at home diagnosis of heart failure events, but they require the patient to visit their physician in the event of an episode in order to receive an injection of heart failure medication in order to prevent hospital admission.

SUMMARY OF THE INVENTION

The present disclosure is directed to a device that improves the ability to monitor pulmonary artery pressures to aid in clinical decision making. For example, there is currently no convenient way to monitor right-side heart strain and pulmonary artery pressures in real time, and current treatment methods typically require long treatment durations to ensure that an embolism has cleared. The longer patients are exposed to medications or treatment solutions that dissolve clots, the greater the risk of internal bleeding. Internal bleeding can be devastating in situations such as intra-cranial hemorrhage. Therefore, determining when the embolism has been sufficiently treated would be advantageous to shorten delivery time for the treatment solution. The apparatus and methods described herein may be used for improving the delivery of treatment solutions to the pulmonary arteries for treatment of pulmonary embolisms. Further, in one embodiment, the apparatus may include a mechanism to detect when healthy blood flow through the pulmonary arteries is reestablished, thereby indicating the treatment is completed.

Thus, in a first aspect, the present disclosure provides an apparatus that includes (a) a first tubular housing defining a first lumen, the first tubular housing having a first end and a second end, wherein the first end of the first tubular housing includes a first exit port, (b) a second tubular housing defining a second lumen, the second tubular housing having a first end and a second end, wherein the first end of the second tubular housing includes a second exit port, (c) a third tubular housing defining a third lumen, the third tubular housing having a first end and a second end, wherein the third tubular housing is coupled to at least one of the first tubular housing and the second tubular housing such that each of the first tubular housing, the second tubular housing, and the third tubular housing are fixed with respect to one another, (d) a first catheter having a first end and a second end, wherein a portion of the first catheter arranged near the first end includes a first plurality of outlets, and wherein the first catheter is configured to be positioned at least partially within the first tubular housing, (e) a second catheter having a first end and a second end, wherein a portion of the second catheter near the first end includes a second plurality of outlets, and wherein the second catheter is configured to be positioned at least partially within the second tubular housing, (f) a pressure transducer line positioned in the third lumen of the third tubular housing, and (g) a pressure transducer coupled to the pressure transducer line.

In a second aspect, the present disclosure also provides a method that includes (a) introducing the apparatus of the first aspect into an arterial configuration via arterial access, (b) advancing the first catheter with respect to the first tubular housing such that the first end of the first catheter exits the first exit port and extends beyond the first end of the first tubular housing, (c) advancing the second catheter with respect to the second tubular housing such that the first end of the second catheter exits the second exit port and extends beyond the first end of the second tubular housing, and (d) advancing a treatment solution out of the first plurality of outlets of the first catheter and the second plurality of outlets of the second catheter and into the arterial configuration.

In a third aspect, the apparatus according to the first aspect of the present disclosure can be coupled to a subcutaneously implantable pump. The pump may include a reservoir which can be filled with a therapeutic or drug solution. When a pressure transducer senses an elevated pulmonary artery pressure, the pressure transducer may communicate with a controller which activates the pump to deliver the therapeutic solution to the pulmonary arteries until the pressure transducer senses an acceptable normal pulmonary artery pressure and communicates with the controller which subsequently modulates the flow rate or turns the pump off. Pulmonary hypertension can also be monitored as a means of detecting episodes of heart failure. As such, aspects of the present disclosure could also be used in conjunction with medications appropriate for heart failure patients. In such an example, when the system detects elevated pulmonary artery pressure, the system will communicate with the pump to infuse heart failure medications.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5A illustrates the first catheter positioned within the first tubular housing and/or the second catheter positioned within the second tubular housing, according to an example embodiment.

FIG. 5B illustrates the first catheter positioned within the first tubular housing and/or the second catheter positioned within the second tubular housing, according to another example embodiment.

FIG. 5C illustrates the first catheter positioned within the first tubular housing and/or the second catheter positioned within the second tubular housing, according to another example embodiment.

DETAILED DESCRIPTION OF THE INVENTION

Figure 1:
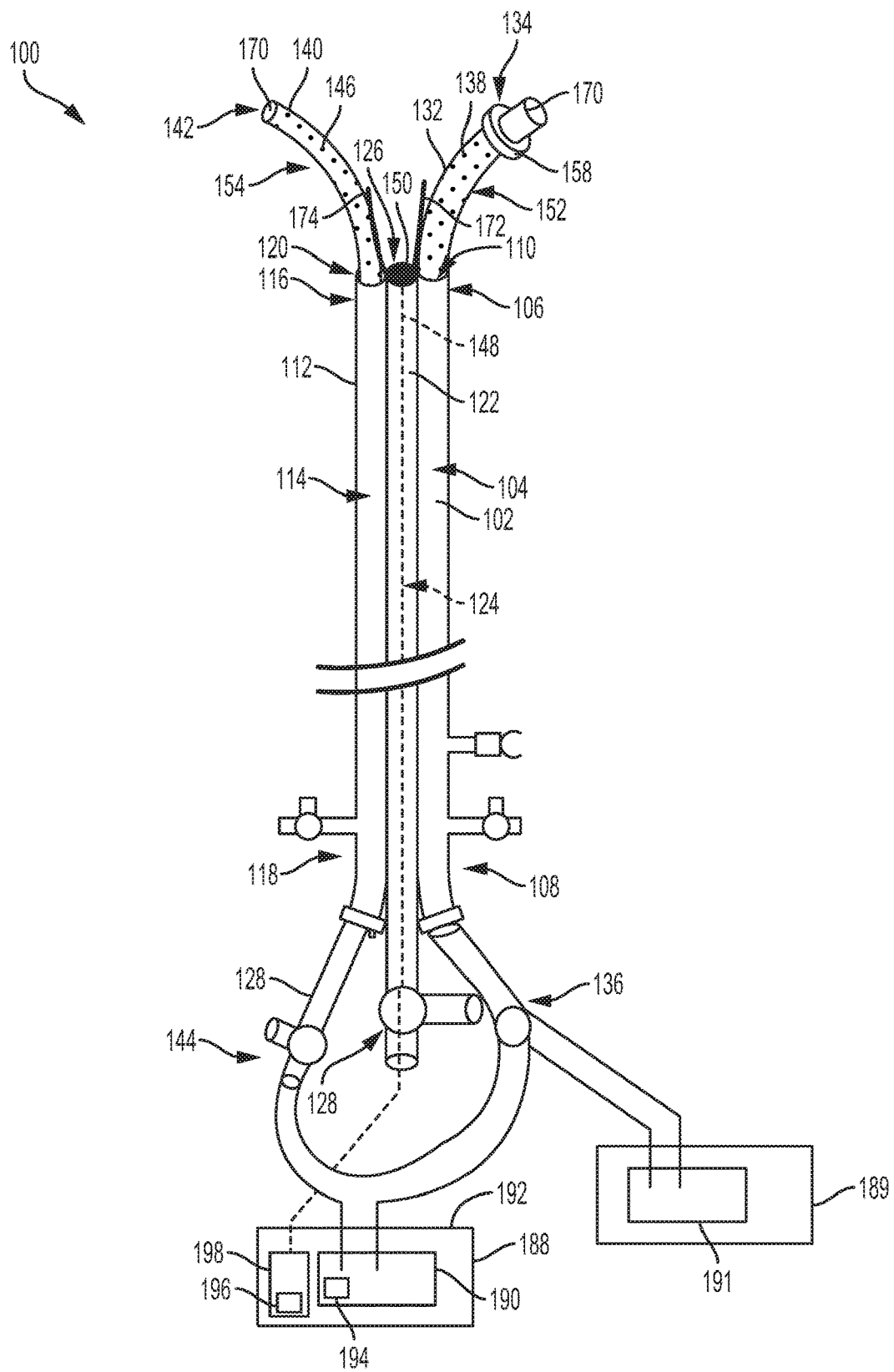
FIG. 1 illustrates an example apparatus, according to an example embodiment.

The description of the different advantageous arrangements are presented for purposes of illustration and description, and are not intended to be exhaustive or limited to the examples in the form disclosed. Many modifications and variations will be apparent to those of ordinary skill in the art. Further, different examples may provide different advantages as compared to other examples. The example or examples selected are chosen and described in order to best explain the principles of the examples, the practical application, and to enable those of ordinary skill in the art to understand the disclosure for various examples with various modifications as are suited to the particular use contemplated.

As used herein, with respect to measurements, "about" means+/−5%.

As used herein, "coupled" means associated directly, as well as indirectly. For example, a member A may be directly associated with a member B, or may be indirectly associated therewith, e.g., via another member C. It will be understood that not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more features, structures, or characteristics described in connection with the example are included in at least one implementation. The phrases "one embodiment" or "one example" in various places in the specification may or may not be referring to the same example.

As used herein, apparatus, element and method "configured to" perform a specified function is indeed capable of performing the specified function without any alteration, rather than merely having potential to perform the specified function after further modification. In other words, the apparatus, element, and method "configured to" perform a specified function is specifically selected, created, implemented, utilized, programmed, and/or designed for the purpose of performing the specified function. As used herein, "configured to" denotes existing characteristics of an apparatus, element, and method which enable the apparatus, element, and method to perform the specified function without further modification. For purposes of this disclosure, an apparatus, element, and method described as being "configured to" perform a particular function may additionally or alternatively be described as being "adapted to" and/or as being "operative to" perform that function.

As used herein, "first end" refers to the end that will be a "distal end" relative to an operator of the apparatus upon deployment in vivo. As such, the "first end" of the apparatus refers to the end of the device (when in use) located nearer the treatment zone (e.g., the pulmonary artery) of the subject.

As used herein, "second end" refers to the end that will be a "proximal end" relative to an operator of the apparatus upon deployment in vivo. As such, the "second end" of the apparatus refers to the end of the device (when in use) located further away from the targeted lumen of the subject and nearer the access site and the operator.

As used herein, a "catheter" is an apparatus that is connected to a deployment mechanism and houses a medical device that can be delivered over a guide wire. The catheter may include a guide wire lumen for over-the-wire guidance and may be used for delivering a stent graft to a target lumen. A catheter can have braided metal strands within the catheter wall to maintain structural integrity. The structural elements of the catheter tip can be bonded or laser welded to the braided strands of the catheter to improve the performance characteristics of the catheter tip.

As used herein, a "guide wire" is an elongated cable comprised of various biocompatible materials including metals and/or polymers. Guide wires may be used for selecting target lumens and guiding catheters to target deployment locations. Guide wires are typically defined as wires used independently of other devices that do not come as part of an assembly.

As used herein, "lumen" refers to a passage within an arterial structure, such as the pulmonary arteries, or stent grafts or the passage within the tubular housings or catheters through which the guide wire may be disposed.

As used herein, "opening" means a diversion point in the catheter that may or may not be in free communication with the exterior of the catheter.

As used herein, all references to the "first opening" and the corresponding structure applies to all subsequent additional openings.

As used herein, "French" refers to a unit of measurement for a catheter. A round catheter of 1 French has an external diameter of ⅓ mm, and therefore the diameter of a round catheter in millimeters can be determined by dividing the French size by 3.

As used herein, "treatment solution" refers to any flowable material that may be administered into the pulmonary artery. When the drug solution comprises a therapeutic to be administered to a patient, any suitable drug that can be administered in solution can be used. As one example, the treatment solution includes lytic agents. In various non-limiting embodiments, the therapeutic may comprise sirolimus, heparin, and cell-based therapies; and antineoplastic, anti-inflammatory, antiplatelet, anticoagulant, antifibrin, antithrombin, antimitotic, antibiotic, vasodisle, antiallergic thrombolytic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), thrombolytic—urokinase, streptokinase, TPA (Tissue Plasminogen Activator) colchicine, proteins, peptides, vasodilators—nitro-based drug, Ca++ channel blocker, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin. Treatment solutions that are of interest for the pulmonary arteries include vasodilators including epoprostenol (Flolan) and iloprost (Ventavis) and endothelin receptor antagonists such as Ambrisentan (Letairis). Additional therapeutic solutions that can be infused into the pulmonary arteries include Sildenafil (Viagra) and Tadalafil (Cialis), high-dose calcium channel blockers including Amlodipine (Norvasc), Diltizem (Cardizem, Tiazac), and Nifedipine (Adalat, Procardia), and various diuretics. Various nitrates for coronary artery disease can also be beneficial when infused, including isosorbide dinitrate (Dilatrate, Isordil), isosorbide mononitrate (ISMO), and nitroglycerine (Nitro-Dur, Nitrolingual, and Nitrostate). Therapeutics that can be infused with the apparatus and methods of the present disclosure for treating heart failure include inotropes such as dabutamine, angiotensin-convertine enzyme inhibitors, angiotensin II receptor blockers, beta blockers, diuretics, aldosterone antagonists, and digoxin. In addition, non-therapeutic fluids, such as water, may be used, if the apparatus is being used in a teaching model or training demonstration for example.

Figure 2A:
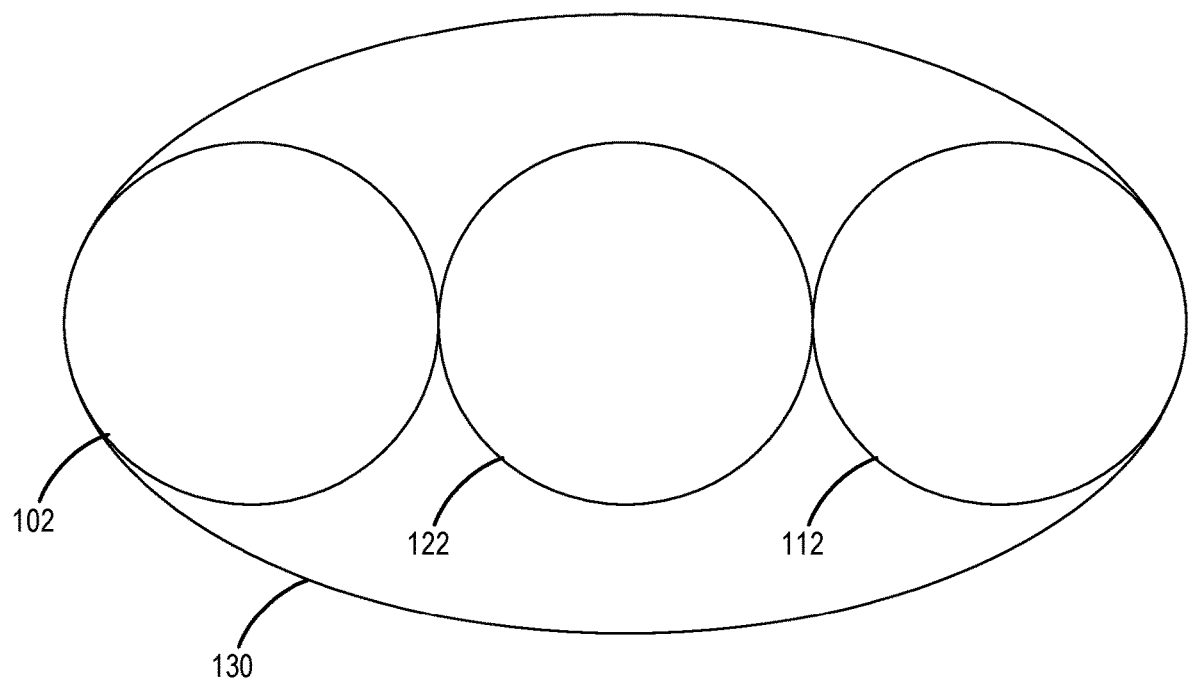
FIG. 2A illustrates a cross-section of one example configuration of the apparatus of FIG. 1, according to one embodiment.
Figure 2B:
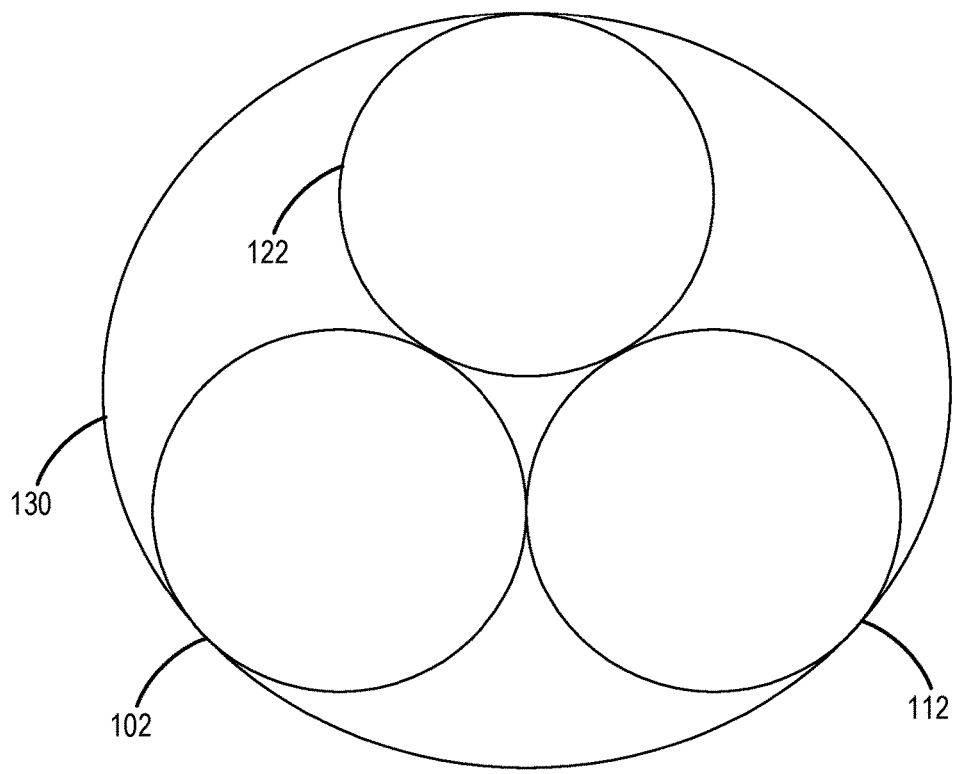
FIG. 2B illustrates a cross-section of another example configuration of the apparatus of FIG. 1, according to one embodiment.

With reference to the Figures, FIG. 1 illustrates one example embodiment of an apparatus 100. In particular, the apparatus 100 includes a first tubular housing 102 defining a first lumen 104. The first tubular housing 102 includes a first end 106 and a second end 108, and the first end 106 of the first tubular housing 102 includes a first exit port 110. The apparatus 100 further includes a second tubular housing 112 defining a second lumen 114. The second tubular housing 112 includes a first end 116 and a second end 118, and the first end 116 of the second tubular housing 112 includes a second exit port 120. The apparatus further includes a third tubular housing 122 defining a third lumen 124. The third tubular housing 122 includes a first end 126 and a second end 128. The third tubular housing 122 is coupled to at least one of the first tubular housing 102 and the second tubular housing 112 such that each of the first tubular housing 102, the second tubular housing 112, and the third tubular housing 122 are fixed with respect to one another. In another embodiment, there is a single tubular housing or sheath 130 having the first lumen 104, the second lumen 114, and the third lumen 124 extending therethrough and arranged parallel to each other, as shown in FIGS. 2A-2B.

As shown in FIG. 1, the apparatus 100 further includes a first catheter 132 having a first end 134 and a second end 136. A portion of the first catheter 132 arranged near the first end 134 includes a first plurality of outlets 138, and the first catheter 132 is configured to be positioned at least partially within the first tubular housing 102. The apparatus 100 further includes a second catheter 140 having a first end 142 and a second end 144. A portion of the second catheter 140 near the first end 142 includes a second plurality of outlets 146, and the second catheter 140 is configured to be positioned at least partially within the second tubular housing 112. The apparatus 100 also includes a pressure transducer line 148 positioned in the third lumen 124 of the third tubular housing 122 and configured to be coupled to a pressure transducer 150.

In some embodiments, the total length of the apparatus 100 may range from about 50 cm to about 500 cm, and preferably from about 50 cm to about 300 cm. In one example, the first plurality of outlets 138 may be defined along the portion of the first catheter 132 arranged near the first end 134 and having a length ranging from about 3 cm to about 40 cm, and the second plurality of outlets 146 are defined along the portion of the second catheter 140 arranged near the first end 142 and extend along a length ranging from about 3 cm to about 40 cm. In one example, the first and second plurality of outlets 138, 146 comprise small holes arranged in series, as one example. Each of the first and second plurality outlets 138, 146 may have a diameter ranging from about 50 µm to about 250 µm. In another embodiment, each of the first and second plurality of outlets 138, 146 may be slots having a width ranging from about 50 µm to about 250 µm, and a length ranging from about 50 µm to about 250 µm.

The first and second plurality of outlets 138, 146 may be configured to enable a treatment solution to pass through the first and second plurality of outlets 138, 146 and into the treatment zone to help dissolve the embolism. Further, the first catheter 132 may have an inner diameter in the range of about 1.5 French to about 15 French, and the second catheter 140 may have an inner diameter in the range of about 1.5 French to about 15 French. In one example, the first catheter 132 and the second catheter 140 have the same diameter. In another example, the first catheter 132 has a diameter that is different than the diameter of the second catheter 140. In one example, the first plurality of outlets 138 defined along the portion of the first catheter 132 arranged near the first end 134 and the second plurality of outlets 146 defined along the portion of the second catheter 140 arranged near the first end 142 are positioned in a helical pattern. Other embodiments are possible as well.

The first end 134, 142 of each of the first catheter 132 and the second catheter 140 may include a curved section 152, 154, as shown in FIG. 1. In one embodiment, the first end 134, 142 of each of the first catheter 132 and the second catheter 140 may comprise a shape memory material that imparts the radius of curvature. The curved sections 152, 154 of each of the first catheter 132 and the second catheter 140 may have a radius of curvature in the range from about 3 cm to about 500 cm. The curved section 152 of the first catheter 132 may help advance and position the first end 134 of the first catheter 132 into a first branch of the pulmonary artery when the apparatus 100 is in use, and the curved section 154 of the second catheter 140 may help advance and position the first end 142 of the second catheter 140 into a second branch of the pulmonary artery when the apparatus 100 is in use.

In one example, the first catheter 132 is configured to move longitudinally within the first tubular housing 102 for a fixed distance. After advancing the fixed distance, the first catheter 132 may be prevented from moving distally relative to the first tubular housing 102. In such an example, the fixed distance may range from about 0 cm to about 100 cm. In another example, the first catheter 132 may have unimpeded longitudinal travel with respect to the first tubular housing 102. Similarly, in one example, the second catheter 140 is configured to move longitudinally within the second tubular housing 112 for a fixed distance. After advancing the fixed distance, the second catheter 140 may be prevented from moving distally relative to the second tubular housing 112. In such an example, the fixed distance may range from about 0 cm to about 100 cm. In another example, the second catheter 140 may have unimpeded longitudinal travel with respect to the second tubular housing 112.

The pressure transducer line 148 may be positioned within the third lumen 124 of the third tubular housing 122, and a pressure transducer 150 may be coupled to the pressure transducer line 148. In one example, the pressure transducer line 148 is moveable with respect to the third tubular housing 122. In one example, the pressure transducer 150 includes a liquid column including the third tubular housing 122. The pressure transducer line 148 may connect the pressure transducer 150 to a power source and/or a computing device configured to transmit and/or display data from the pressure transducer 150. The pressure transducer 150 may be positioned in a variety of locations. In one example, the pressure transducer 150 may be positioned at the first end of the third tubular housing 122. In another example, the pressure transducer 150 may extend beyond the first end 126 of the third tubular housing 122 and into the pulmonary artery when the apparatus 100 is in use. Such a location may be proximal to the first end 134 of the first catheter 132 when the first catheter 132 is in a deployed position. Other locations for the pressure transducer 150 are contemplated as well. As such, the pressure transducer 150 may be advantageously monitored to observe pulmonary artery pressure within a tolerance thereby indicating treatment completion. Pulmonary artery pressure may become elevated during some cases of pulmonary obstruction and may be a good indicator of hemodynamic stability and hence, treatment completion or lack thereof. For example, normal pulmonary artery pressures would indicate treatment completion.

Figure 3:
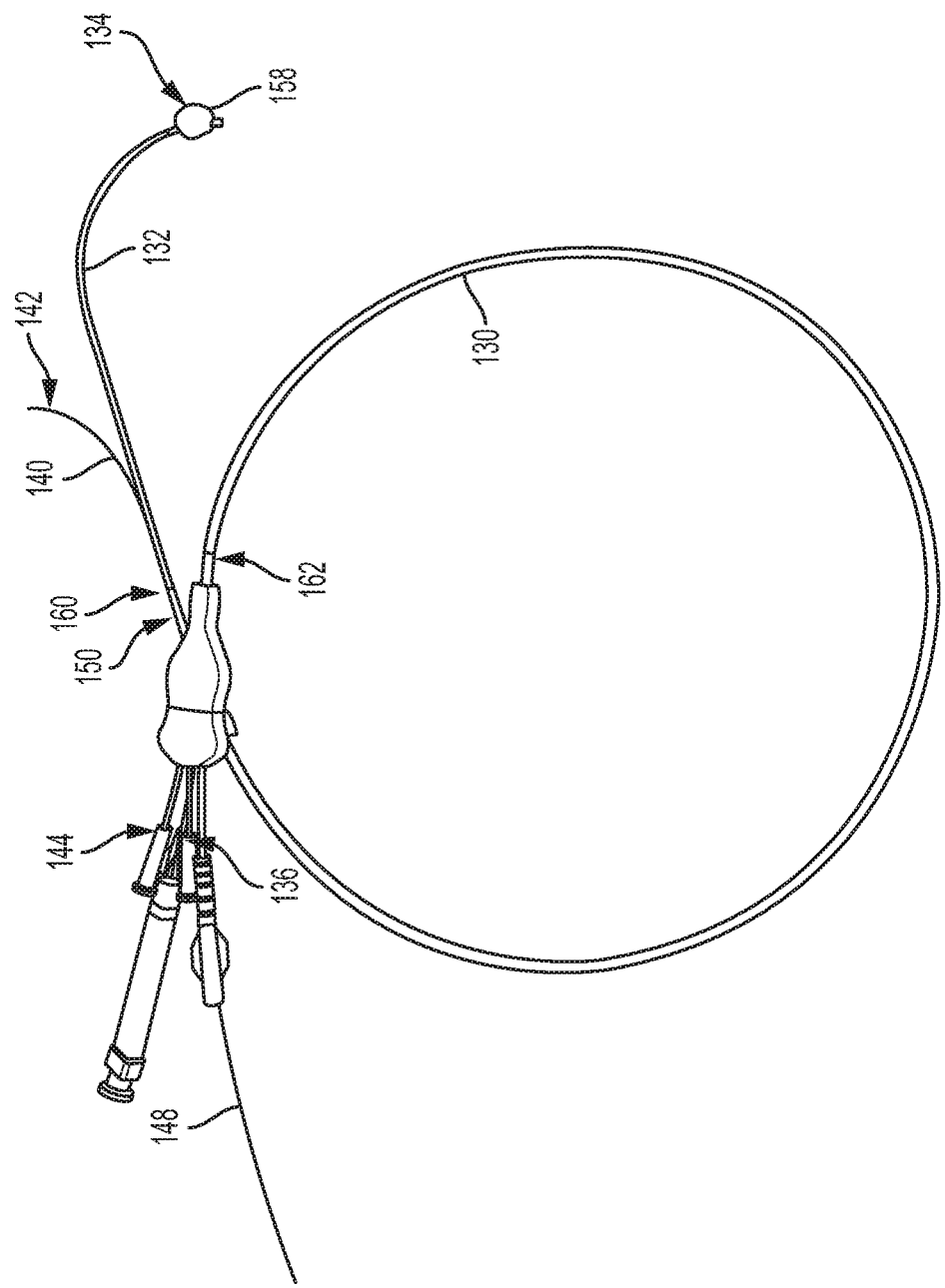
FIG. 3 is a perspective view of the apparatus of FIG. 1, according to an example embodiment.

In one embodiment, as shown in FIG. 1, the apparatus 100 may further include a balloon 158 coupled to the first end 134 of the first catheter 132. In another embodiment, the apparatus 100 may include a sheath 130 having a first end 160 and a second end 162, the sheath positioned around each of the first tubular housing 102, the second tubular housing 112, and the third tubular housing 122, as shown in FIGS. 2A-2B and 3. In one such embodiment, the balloon 158 may be coupled to the first end 160 of the sheath 130, as shown in FIG. 3. In yet another embodiment, the balloon 158 may be coupled to one of the first end 106 of the first tubular housing 102, the first end 116 of the second tubular housing 112, or the first end 126 of the third tubular housing 122.

The arrangement of the first tubular housing 102, the second tubular housing 112, and the third tubular housing 122 may take various forms. FIG. 2A illustrates a cross-section of the apparatus 100, according to one embodiment. As shown in FIG. 2A, the first tubular housing 102, the second tubular housing 112, and the third tubular housing 122 may be positioned in a substantially side-by-side configuration. FIG. 2B illustrates a cross-section of the apparatus 100, according to another embodiment. As shown in FIG. 2B, the first tubular housing 102, the second tubular housing 112, and the third tubular housing 122 may be positioned in a triangular configuration, thereby reducing the overall width of the apparatus 100. Other arrangements are possible as well.

Figure 4C:
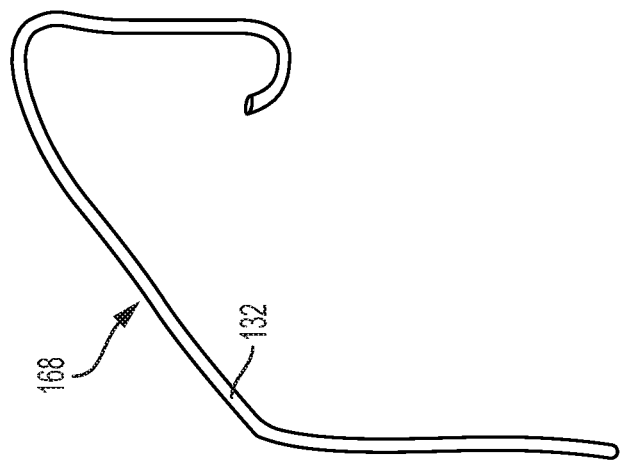
FIG. 4C illustrates the first end of the first catheter and/or the second catheter, according to another example embodiment.
Figure 4B:
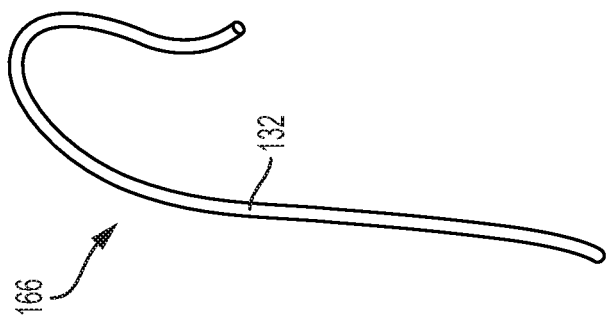
FIG. 4B illustrates the first end of the first catheter and/or the second catheter, according to another example embodiment.
Figure 4A:
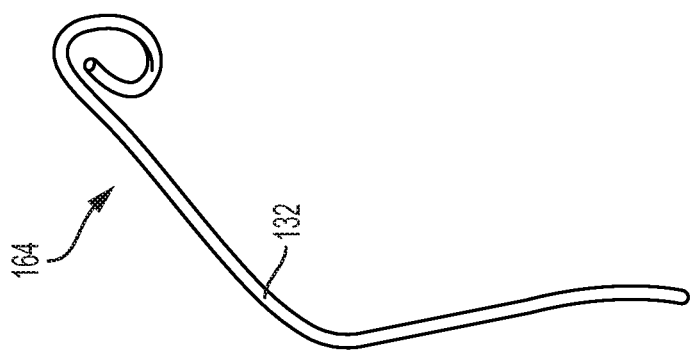
FIG. 4A illustrates the first end of the first catheter and/or the second catheter, according to an example embodiment.

The first end 134, 142 of the first catheter 132 and/or the second catheter 140 may take a variety of forms, as shown in FIGS. 4A-4C. In particular, the first end 134 of the first catheter 132 and/or the first end 142 of the second catheter 140 may have one of an angled pigtail shape 164 (shown in FIG. 4A), a shepherd's hook shape 166 (shown in FIG. 4B), or an angled hook shape 168 (shown in FIG. 4C). Other embodiments are possible as well.

The first catheter 132 and the second catheter 140 may be independently moveable between the pre-deployment position and a deployed position. In such an example, the first end 134 of the first catheter 132 is positioned substantially within the first tubular housing 102 when the first catheter 132 is in the pre-deployment position, and the first end 142 of the second catheter 140 is positioned substantially within the second tubular housing 112 when the second catheter 140 is in the pre-deployment position. In such an embodiment, the first end 134 of the first catheter 132 is configured to extend out of the first exit port 110 when the first catheter 132 is in the deployed position, and the first end 142 of the second catheter 140 is configured to extend out of the second exit port 120 when the second catheter 140 is in the deployed position.

The pre-deployment position may be used during advancement to or placement of the apparatus 100 at the treatment zone, while the deployed position may be used for infusion of treatment solution through the first plurality of outlets 138 of the first catheter 132 and the second plurality of outlets 146 of the second catheter 140. Once the first and second catheters 132, 140 have been moved into the deployed position, the treatment solution may then be advanced through the first and second catheters 132, 140 and infused through the first and second plurality of outlets 138, 146 into the treatment zone. Each of the first and second catheters 132, 140 may include a hemostatic valve 170 within the portion of the first and second catheter 132, 140 arranged near the first end 134, 142 that may allow the treatment solution to pass out through the first and second plurality of outlets 138, 146, but minimize back flow of blood into the first and second catheters 132, 140. Such an embodiment may prevent blood from entering the first and second plurality of outlets 138, 146 and clotting over time, thereby maintaining the infusing ability of the first and second catheters 132, 140. As the multiple emboli are lysed (i.e., dissolved) via the treatment solution, normal blood flow through the pulmonary arteries may be reestablished and may reduce pulmonary artery pressure and increase systemic arterial pressure bringing the patient back to hemodynamic stability.

In one embodiment, shown in FIG. 1, the apparatus 100 may further include a first catheter diverter 172 configured to at least partially obstruct the first lumen 104 of the first tubular housing 102, such that the first catheter 132 contacts the first catheter diverter 172 and is thereby directed at an angle through the first exit port 110 of the first tubular housing 102 when transitioning from the pre-deployment position to the deployed position. The apparatus 100 may further include a second catheter diverter 174 configured to at least partially obstruct the second lumen 114 of the second tubular housing 112, such that the second catheter 140 contacts the second catheter diverter 174 and is thereby directed at an angle through the second exit port 120 of the second tubular housing 112 when transitioning from the pre-deployment position to the deployed position. In such an embodiment, the first catheter diverter 174 may take the form of a first angled tab extending from the first end 106 of the first tubular housing 102 at an angle with respect to a longitudinal axis of the first tubular housing 102, and the second catheter diverter 174 may take the form of a second angled tab extending from the first end 116 of the second tubular housing 112 at an angle with respect to a longitudinal axis of the second tubular housing 112. The angled tabs of the first and second catheter diverters 172, 174 may be flexible to enable the first and second catheters 132, 140 to contact the first and second catheter diverters 172, 174 and thereby be directed out of the first and second exit ports 110, 120. The angle of the first and second catheter diverters 172, 174 may help direct the first and second catheters 132, 140 into opposite branches of the pulmonary artery when in use.

In one embodiment, the first exit port 110 and the second exit port 120 are angled away from each other so as to direct the first catheter 132 and the second catheter 140 in relative opposite directions. In one particular example, a longitudinal axis extending through a center of the first exit port 110 is arranged at an angle relative to a longitudinal axis extending through a center of the second exit port 120. In such an embodiment, the angle between the longitudinal axis of the first exit port 110 and the longitudinal axis of the second exit port 120 ranges from about 15 degrees to about 180 degrees.

In another embodiment, as shown in FIGS. 5A-5C, a shape of the first catheter 132 may be complementary to a shape of the first tubular housing 102 such that the first catheter 132 cannot rotate with respect to the first tubular housing 102 as the first catheter 132 moves longitudinally with respect to the first tubular housing 102. Similarly, a shape of the second catheter 140 may be complementary to a shape of the second tubular housing 112 such that the second catheter 140 cannot rotate with respect to the second tubular housing 112 as the second catheter 140 moves longitudinally with respect to the second tubular housing 112. In particular, as shown in FIGS. 5A-5C, the first catheter 132 and/or the second catheter 140 may be oval-shaped (shown in FIG. 5A), square-shaped (shown in FIG. 5B), or may include one or more ribs 176 extending axially away from a midline of the first catheter 132 and/or the second catheter 140 (shown in FIG. 5C). In such embodiment, the first tubular housing 102 and/or the second tubular housing 112 may be oval-shaped (shown in FIG. 5A), square-shaped (shown in FIG. 5B), or may include one or more outwardly extending protrusions 178 configured to receive the one or more ribs 176 extending axially away from a midline of the first catheter 132 and/or the second catheter 140. Such embodiments may help ensure that the first catheter 132 and/or second catheter 140 are arranged in a proper position to project into the branches of the pulmonary artery in the deployed position.

Figure 5D:
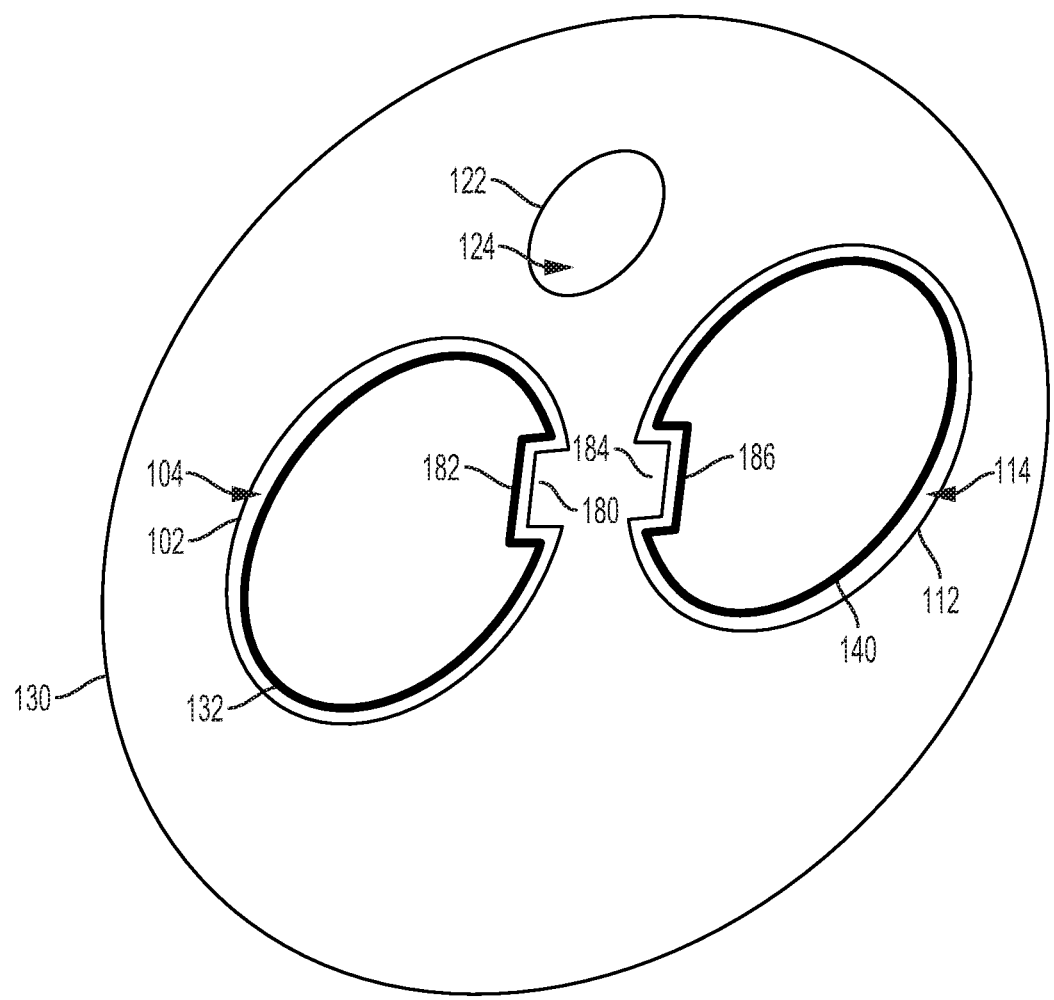
FIG. 5D illustrates the first catheter positioned within the first tubular housing and/or the second catheter positioned within the second tubular housing, according to another example embodiment.

In another example, as shown in FIG. 5D, the apparatus 100 may further include a first rail 180 positioned in the first lumen 104 of the first tubular housing 102. The first rail 180 is configured to mate with a corresponding rail 182 positioned on an external surface of the first catheter 132. In such an embodiment, the apparatus 100 may further include a second rail 184 positioned in the second lumen 114 of the second tubular housing 112. The second rail 184 is configured to mate with a corresponding rail 186 positioned on an external surface of the second catheter 140. Similar to the embodiments described above in relation to FIGS. 5A-5C, the embodiments of FIG. 5D may help ensure that the first catheter 132 and/or second catheter 140 are arranged in a proper position to project into the branches of the pulmonary artery in the deployed position.

Figure 6A:
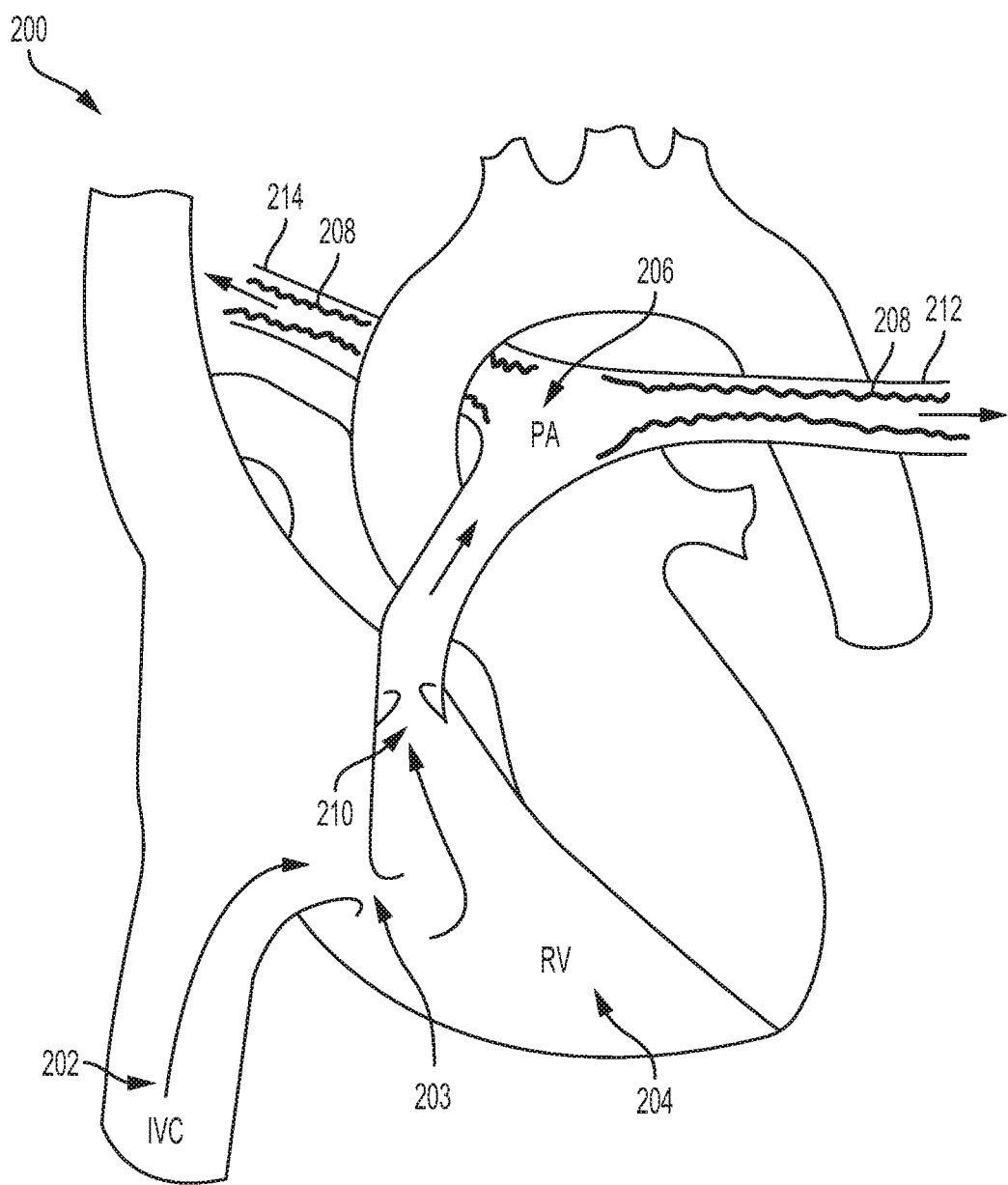
FIG. 6A illustrates a schematic of the cardiopulmonary structure.
Figure 6B:
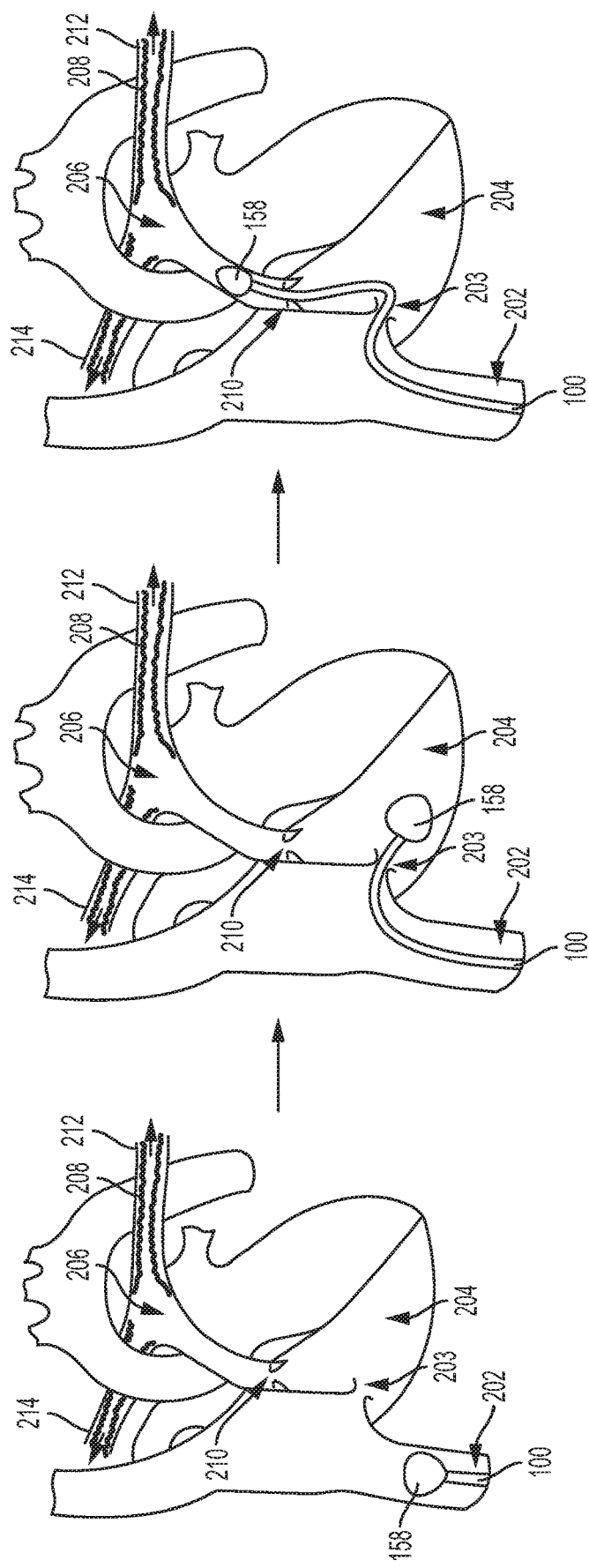
FIG. 6B illustrates the cardiopulmonary structure of FIG. 6A with the apparatus of FIG. 1 positioned herein.

In operation, the apparatus 100 may be positioned in the treatment zone via a balloon, via a guidewire, or via some other means. In particular, FIG. 6A illustrates a schematic of the cardiopulmonary structure, including a heart 200, and blood flow through the inferior vena cava (IVC) 202, right ventricle (RV) 204, and pulmonary artery (PA) 206 with emboli 208 occluding the pulmonary artery 206. FIG. 6B illustrates an example embodiment including a balloon 158 coupled to the distal end of the apparatus 100. As shown in FIG. 6B, the apparatus 100 may be advanced manually or pulled through the inferior vena cava by the balloon 158 via blood flow. In one example, such a balloon 158 may be a sail balloon. The balloon 158 may be coupled to the distal end of the apparatus 100, or coupled to the first end 134 of the first catheter 132 as discussed above and as shown in FIG. 1. Once the balloon 158 has entered the inferior vena cava 202, the balloon 158 may then continue through the tricuspid valve 203 and into the right ventricle 204. Finally, the balloon 158 may be advanced through the pulmonary valve 210 along with the apparatus 100. The operator may observe the advancement of the apparatus 100 on a fluoroscopic image and may stop advancement once the apparatus 100 is disposed in the pulmonary artery 206 near the embolism 208.

Figure 6C:
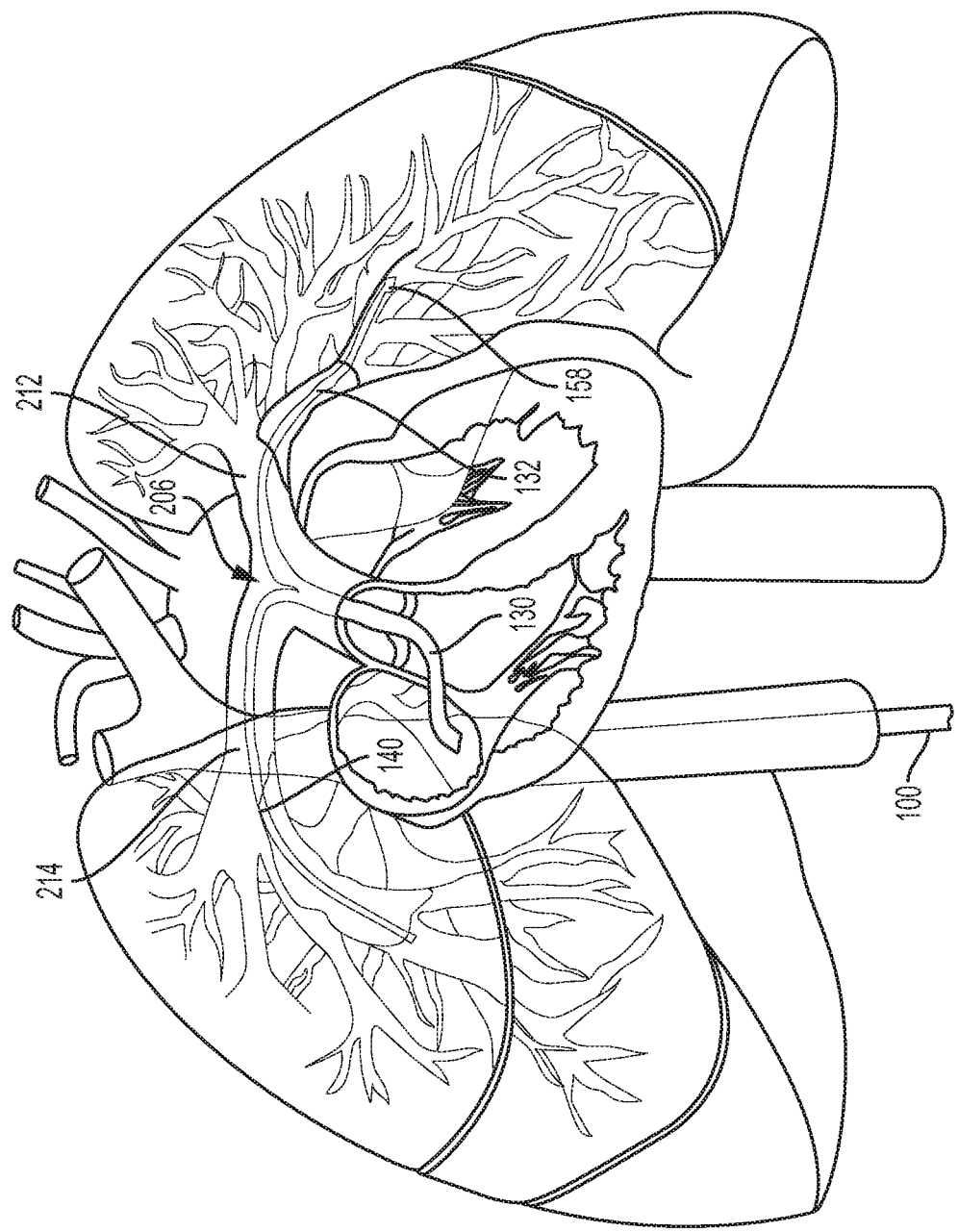
FIG. 6C illustrates in the apparatus of FIG. 1 in the deployed position in the cardiopulmonary structure.

Once the apparatus 100 is disposed in the pulmonary artery 206 near the embolism 208, the first catheter 132 may be directed out of the first exit port 110 of the first tubular housing 102 until the first end 134 of the first catheter 132 is positioned within a first branch 212 of the pulmonary artery 206. The curved section 152 of the first catheter 132 may aid in positioning the first end 134 of the first catheter 132 into the first branch 212 of the pulmonary artery 206. The second catheter 140 may then be advantageously directed through the second exit port 120 of the second tubular housing 112, and into a second branch 214 of the pulmonary artery 206. The apparatus 100 is shown in the deployed position in FIG. 6C.

Once positioned in the desired vasculature, the treatment solution may then be infused through the first and second plurality of outlets 138, 146 of the first and second catheters 132, 140, respectively, into the treatment zone, as discussed above. The apparatus 100 may further include a pressure transducer line 148 positioned in the third lumen 124 of the third tubular housing 122 and configured to be coupled to a pressure transducer 150. As discussed above, the pressure transducer 150 may advantageously monitor and observe pulmonary pressure until the pulmonary pressure decreases below a tolerance, thereby indicating treatment completion.

Figure 7:
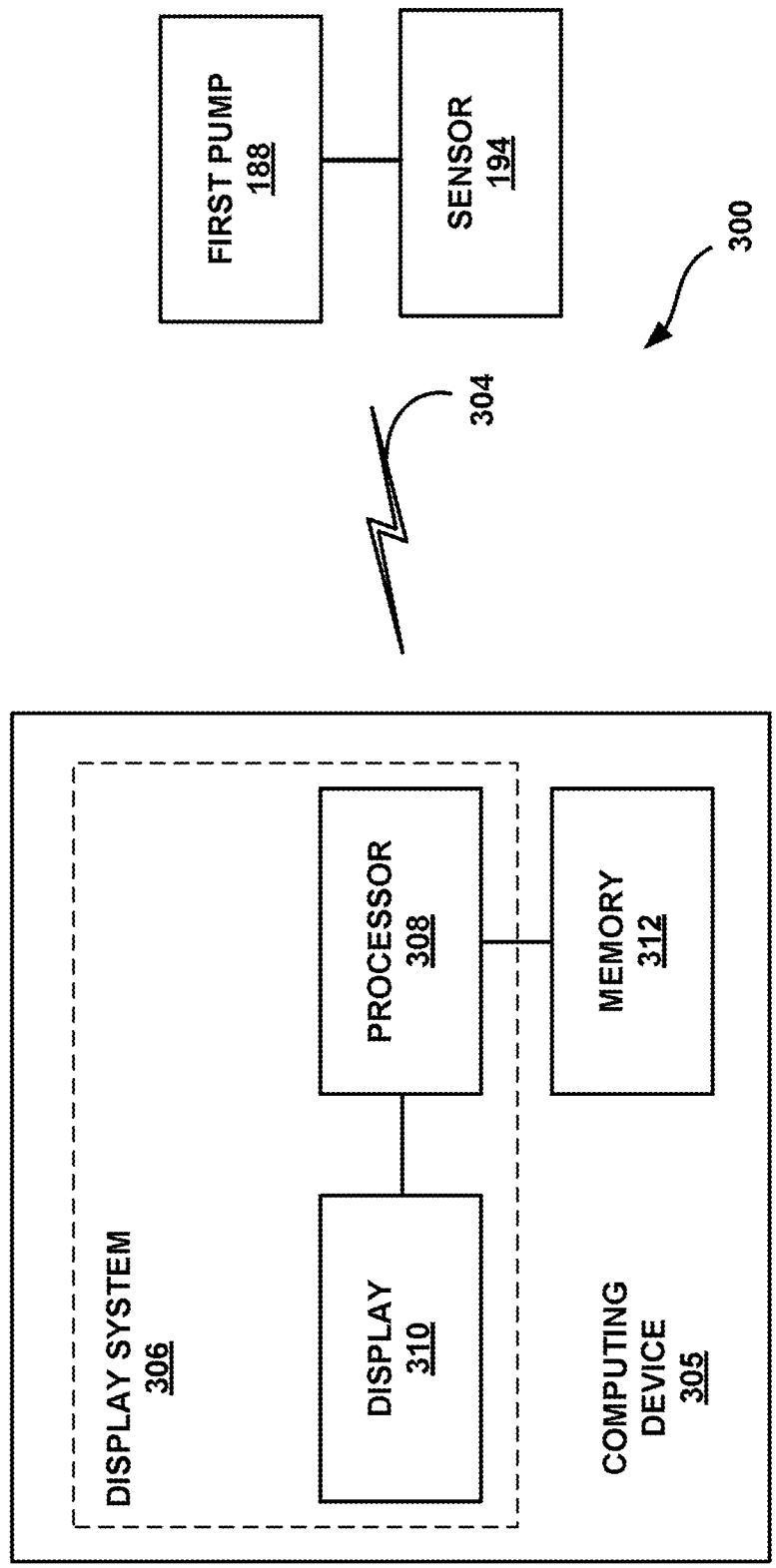
FIG. 7 is a schematic drawing of a computer network infrastructure, according to an example embodiment.

In yet another embodiment shown in FIGS. 1 and 7, the apparatus 100 may further include a first pump 188 coupled to at least one of the first catheter 132 and the second catheter 140, and a reservoir 190 coupled to the first pump 188. In particular, the first pump 188 may be configured for fluid communication with the first catheter 132 and/or the second catheter 140. In one embodiment, the apparatus 100 may further include a housing 192 positioned around the first pump 188 and the reservoir 190. The housing 192 may include a biocompatible outer surface. The reservoir 190 may be configured to hold a treatment solution for delivery to the pulmonary artery via the first pump 188. The first and second catheters 132, 140 may be coupled to the first pump 188 via a press fit friction connection with an external locking ring, among other options for attachment. The pressure transducer 150 is in electronic communication with the first pump 188, such that the pressure transducer 150 is conductively coupled to the first pump 188.

Treatment solutions that are of interest for the pulmonary arteries include vasodilators including epoprostenol (Flolan) and iloprost (Ventavis) and endothelin receptor antagonists such as Ambrisentan (Letairis). Additional therapeutic solutions that can be infused into the pulmonary arteries include Sildenafil (Viagra) and Tadalafil (Cialis), high-dose calcium channel blockers including Amlodipine (Norvasc), Diltizem (Cardizem, Tiazac), and Nifedipine (Adalat, Procardia), and various diuretics. Various nitrates for coronary artery disease may also be beneficial when infused, including isosorbide dinitrate (Dilatrate, Isordil), isosorbide mononitrate (ISMO), and nitroglycerine (Nitro-Dur, Nitrolingual, and Nitrostate). Therapeutics that may be infused with the present disclosure for treating heart failure include inotropes such as dabutamine, angiotensin-convertine enzyme inhibitors, angiotensin II receptor blockers, beta blockers, diuretics, aldosterone antagonists, and digoxin.

In one example, the first pump 188 and reservoir 190 may be positioned outside of the body of the patient. In another example, the apparatus 100, first pump 188, and reservoir 190 may be implantable within the patient. In particular, the first pump 188 and reservoir 190 may be positioned subcutaneously in a pocket between the skin and the muscle of the patient or in or beneath a fat pocket of the patient, for example. In example embodiments, the first pump 188 and reservoir 190 may be positioned in the abdomen, buttock or thigh of the patient. Other example locations are possible as well. The first pump 188 may include a transcutaneously accessible reservoir for refilling the treatment solution. This may be done via palpable transcutaneous markers and ultrasound- or fluoroscopic-guidance when the patient is seen for follow-up.

The apparatus 100 may further include a sensor 194 positioned in the reservoir 190. The sensor 194 is configured to determine a volume of treatment solution remaining in the reservoir 190. The apparatus 100 may also include a wireless communication interface 196 in communication with the sensor 194. The wireless communication interface 196 is configured to transmit the determined volume, along with other information, to a local or remote computing device.

Further, the apparatus 100 may include a controller 198 coupled to the first pump 188, the controller having a processor. The controller 198 may be coupled to the pressure transducer 150 via the pressure transducer line 148. In such an embodiment, the pressure transducer 150 will communicate with the first pump 188 so that the controller 198 may register the pressures sensed by the pressure transducer 150. In particular, the controller 198 may include a wireless communication interface 196 that transmits information received from the pressure transducer 150, along with other information, to a local or remote computing device, as discussed above. Thus, the controller 198 may be configured to (i) determine if, via the pressure transducer 150, a pulmonary artery blood pressure is greater than a threshold value, and (ii) in response to the determination that the pulmonary artery blood pressure is greater than the threshold value, activate the first pump 188 to advance the treatment solution from the reservoir 190 to the first plurality of outlets 138 of the first catheter 132 and the second plurality of outlets 146 of the second catheter 140. The first pump 188 may also include a sensor 194 configured to determine the level of the therapeutic solution remaining in the reservoir 190, as discussed above. The sensor 194 may be in communication with the controller 198, and the wireless communication interface 196 may be configured to transmit the determined volume to a local or remote computing device, such as a physician's computer. The physician may therefore monitor when the treatment solution is almost empty, and may contact the patient to schedule a time to refill the reservoir 190.

Further, the controller 198 may be configured to (i) determine, via the pressure transducer 150, that a blood pressure is less than the threshold value, and (ii) in response to the determination that the blood pressure is less than the threshold value, either modulate the flow rate accordingly or deactivate the first pump 188. In one particular example, the apparatus 100 may include a first pump 188 coupled to the first catheter 132, and a second pump 189 coupled to the second catheter 140. In such an example, the controller 198 may be configured to activate and deactivate the first and second pumps 188, 189 independently of one another. Further, in such an example the apparatus 100 may include a first reservoir 190 coupled to the first pump 188, and a second reservoir 191 coupled to the second pump 189. The first and second reservoirs 190, 191 may contain the same treatment solution, or the treatment solution in the first reservoir 190 may be different than the treatment solution in the second reservoir 191. When there are two or more reservoirs, the access site for each reservoir may include clearly discernible markers for the purposes of refilling so that the wrong medication is not added to the wrong reservoir. For example, each of the first reservoir 190 and the second reservoir 191 may include a unique identifier such as a stamp or a radiopaque marker. In another example, the unique identifier may be a shape of the first reservoir 190 and the second reservoir 191, such that the first reservoir 190 has a different shape than the second reservoir 191. In another example, each reservoir may include a unique coupling mechanism to a corresponding catheter. Other examples are possible as well.

In one example, the pressure transducer 150, the sensor 194, and/or the pump(s) 188, 189 may be operated periodically in order to save power and extend battery life. For instance, if a treatment solution has a long acting characteristic, the pump(s) 188, 189 could be programmed to turn on only after the treatment solution is believed to be fully metabolized or become inactive. Additionally, heart failure episodes develop over a relatively long period of time, up to 60 days, with gradually increasing pulmonary artery pressure along the way, so the sensor 194 could be turned on in a delayed frequency which allows for conservation of the battery. The sensor 194 could be constructed as a microelectromechanical system so that the sensor 194 may be remotely charged with radio frequency methods. Alternatively, the pump(s) 188, 189 may be charged using energy harvesting methodologies wherein a flexible integrated device may be laid on an organ such as the heart or lungs in order to harvest the mechanical energy for charging the battery on the sensor 194 or the pump(s) 188, 189. The pump(s) 188, 189 may be made by layering piezoelectric material such as lead zirconate titanate onto flexible silicone with added rectifiers and batteries, in one example.

Further, the pump(s) 188, 189 may be biocompatible and blood compatible. Proper hermetic encapsulation is required to protect the electronics from water intrusion that can result in sensor drift and device failure. Hermetic encapsulation is also required to prevent the ingress of oxygen which may oxidize metal connections such as solders and lead to attachment failure. The sensor 194 may also manage the immune response occurring at the surface to prevent fibrous tissue encapsulation or other cellular or blood-based biofouling. The pressure transducer 150 may be made from a membrane and a sealed cavity. With one membrane element responding to and deflecting under pressure and the other membrane being placed on the bottom rigid surface within the vacuum sealed cavity. Deflection of the membrane may cause changes in the capacitance measured between the electrode pair. Alternatively, piezoresistive sensing may allow for a piezoresistor to be patterned onto the membrane surface, and deflection of the membrane may be transduced into a change in resistance, usually measured via a bridge circuit. The membrane exposed to blood may be designed with surface properties to resist protein adsorption and ultimately biofouling. Other embodiments are possible as well.

The apparatus 100 described herein may be used to treat pulmonary hypertension or heart failure of a patient. Pulmonary hypertension begins when tiny arteries in the lungs, called pulmonary arteries, and capillaries become narrowed, blocked, or destroyed. This makes it harder for blood to flow through your lungs, and raises pressure within your lungs' arteries. Ordinarily, the blood flows easily through the vessels in your lungs, so blood pressure is usually much lower in your lungs. With pulmonary hypertension, the rise in blood pressure may be caused by changes in the cells that line your pulmonary arteries. These changes may cause extra tissue to form, eventually narrowing or completely blocking the blood vessels, making the arteries stiff and narrow. This may impede blood to flow, thereby raising the blood pressure in the pulmonary arteries.

Thus, the treatment solution may take various forms to help treat pulmonary hypertension. Endothelins are peptides that constrict blood vessels and raise blood pressure. Overproduction of endothelin in the lungs may cause pulmonary hypertension, which may sometimes be treated with endothelin receptor antagonists, such as bosentan, sitaxentan, or ambisentan. Inhaled epoprostenol may reduce pulmonary pressure through vasodilation. A dose of 60 micrograms is hemodynamically safe and typically completely reverses after 25 minutes. In one embodiment, less than 60 micrograms of the endothelin receptor antagonist can be released from the pump(s) 188, 189, through the first and second catheters 132, 140, and into the pulmonary vasculature reducing the pulmonary artery pressure. Once the pulmonary artery pressure is reduced below the threshold value, delivery of the drug may cease. The effects will likely reverse in about 25 minutes. If pulmonary artery pressure again increases after the drug reverses, the pump(s) 188, 189 may release more treatment solution from the reservoir. Several therapeutic drugs can be used with the pump(s) 188, 189 and apparatus 100, and this application should not be limited to endothelin receptor antagonists. An alternative drug that could be used is Ventavis. Ventavis is traditionally inhaled every three hours. In this alternative embodiment, when pulmonary artery pressure increases above the threshold value, the Ventavis may be released effectively reducing the pulmonary artery pressure. Other treatment solutions for treating pulmonary hypertension are possible as well.

Further, the treatment solution may take various forms to help treat heart failure. Angiotensin-converting enzyme (ACE) inhibitors are a vasodilator, a drug that widens blood vessels to lower blood pressure, improve blood flow and decrease the workload on the heart. Examples include enalapril (Vasotec), lisinopril (Zestril) and captopril (Capoten). Angiotensin II receptor blockers are drugs, which include losartan (Cozaar) and valsartan (Diovan), have many of the same benefits as ACE inhibitors. They may be an alternative for people who can't tolerate ACE inhibitors. Beta blockers are a class of drugs that slow heart rate and reduce blood pressure and also limits or reverses some of the damage to the heart in the event of systolic heart failure. Examples include carvedilol (Coreg), metoprolol (Lopressor) and bisoprolol (Zebeta). These medicines reduce the risk of some abnormal heart rhythms and lessen the chance of dying unexpectedly. Beta blockers may reduce signs and symptoms of heart failure, improve heart function, and increase longevity. Diuretics are drugs that cause frequent urination and keep fluid from collecting in the body. Diuretics, such as furosemide (Lasix), may also decrease fluid in the lungs to ease breathing. Aldosterone antagonists are drugs that include spironolactone (Aldactone) and eplerenone (Inspra). These are potassium-sparing diuretics, which may also have additional properties that may help people with severe systolic heart failure live longer. Inotropes are intravenous medications used in people with severe heart failure in the hospital to improve heart pumping function and maintain blood pressure. Digoxin (Lanoxin), also referred to as digitalis, is a drug that increases the strength of the heart muscle contractions. Digoxin also tends to slow the heartbeat. Digoxin reduces heart failure symptoms in systolic heart failure and typically may be given to someone with a heart rhythm problem, such as atrial fibrillation. Other treatment solutions for treating heart failure are possible as well.

FIG. 7 illustrates an example schematic drawing of a computer network infrastructure. In one system 300, a computing device 305 communicates with the first pump 188 using a communication link 304, such as a wired or wireless connection. The computing device 305 may be any type of device that may receive data and display information corresponding to or associated with the data. For example, the computing device 305 may be a mobile phone, a tablet, a smart watch, or a personal computer, as examples.

Thus, the computing device 305 may include a display system 306 that includes a processor 308 and a display 310. The display 310 may be, for example, an optical see-through display, an optical see-around display, or a video see-through display. The processor 308 may receive data from the first pump 188, and configure the data for display on the display 310. In another embodiment, the processor 308 may receive data from the one or more sensors 194, and configure the data for display on the display 310. Depending on the desired configuration, processor 308 can be any type of processor including, but not limited to, a microprocessor, a microcontroller, a digital signal processor, or any combination thereof.

The computing device 305 may further include on-board data storage, such as memory 312 coupled to the processor 308. The memory 312 may store software that can be accessed and executed by the processor 308, for example. The memory 312 can include any type of memory now known or later developed including but not limited to volatile memory (such as RAM), non-volatile memory (such as ROM, flash memory, etc.) or any combination thereof.

According to an example embodiment, the computing device 305 may include program instructions that are stored in the memory 312 (and/or possibly in another data-storage medium) and executable by the processor 308 to facilitate the various functions described herein. Although various components of the system 300 are shown as distributed components, it should be understood that any of such components may be physically integrated and/or distributed according to the desired configuration of the computing system.

The first pump 188 and the computing device 305 may contain hardware to enable the communication link 304, such as processors, transmitters, receivers, antennas, etc.

In FIG. 7, the communication link 304 is illustrated as a wireless connection; however, wired connections may also be used. For example, the communication link 304 may be a wired link via a serial bus such as a universal serial bus or a parallel bus. A wired connection may be a proprietary connection as well. The communication link 304 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. Such a communication link 504 may have a frequency band in the range of 402-405 MHz or greater than 2 GHz.

As such, the first pump 188 and or the sensor 194 could have wireless communication capabilities for transmitting data to the patient's physician regarding power consumption, current reservoir levels, remaining power levels, infusion rates, and pressure measurements over time. Further, such a wireless communication system may be designed such that the microcontroller and non-volatile storage of the pump 188 are not damaged by x-rays and the wireless communication system 300 does not cause dielectric heating during MRI examinations.

In such a system 300, the first pump 188 will be able to communicate with the computing device 305, and the computing device 305 may register the reservoir's therapeutic solution level as well as the estimated time remaining until a refill is required. The first pump 188 may also register and transmit a summary of time-based pulmonary artery pressures in addition to dose responses of the pulmonary artery pressures over a given time period to the computing device 305. The first pump 188 will also be able to communicate with the computing device 305 to register the pump battery's remaining power level as well as the current average power consumption rate. The computing device 305 may then transmit this information to the physician remotely to encourage better patient-physician care management. In addition, the first pump 188 may wirelessly or remotely gather information such as oxygen saturation, system blood pressure, (actual or relative) and adjust medication output from the first pump 188 or pumps 188, 189 by either turning on or off the first pump 188. This information may be recorded, stored, and transmitted wirelessly by the first pump 188 and/or computing device 305.

It may be clinically useful for patients who have pulmonary hypertension or heart failure to have additional patient information tracked such as blood pressure, heart rate, and oxygen saturation. In one embodiment, a patient who had an implanted apparatus 100 and first pump 188 would also have a wearable device, such as computing device 305, that could monitor blood pressure, heart rate, and/or oxygen saturation. The computing device 305 could communicate with the first pump 188 via wireless communication link 304, and data could be stored either on the first pump 188 or on the computing device 305. The information could also be transmitted to the physician periodically or downloaded on the physician's PC when the patient is seen for a follow-up appointment. In such an embodiment, the first pump 188 may be controlled with inputs of heart rate, blood pressure, and oxygen saturation in addition to the pulmonary artery pressures as well as the medication infusion rates. In another potential embodiment, the first pump 188 may have a safety feature that deactivates the first pump 188 if it does not receive the aforementioned inputs. In this scenario, a warning message will be sent to the display 310 of the computing device 305 and/or the patient's physician.

Figure 8:
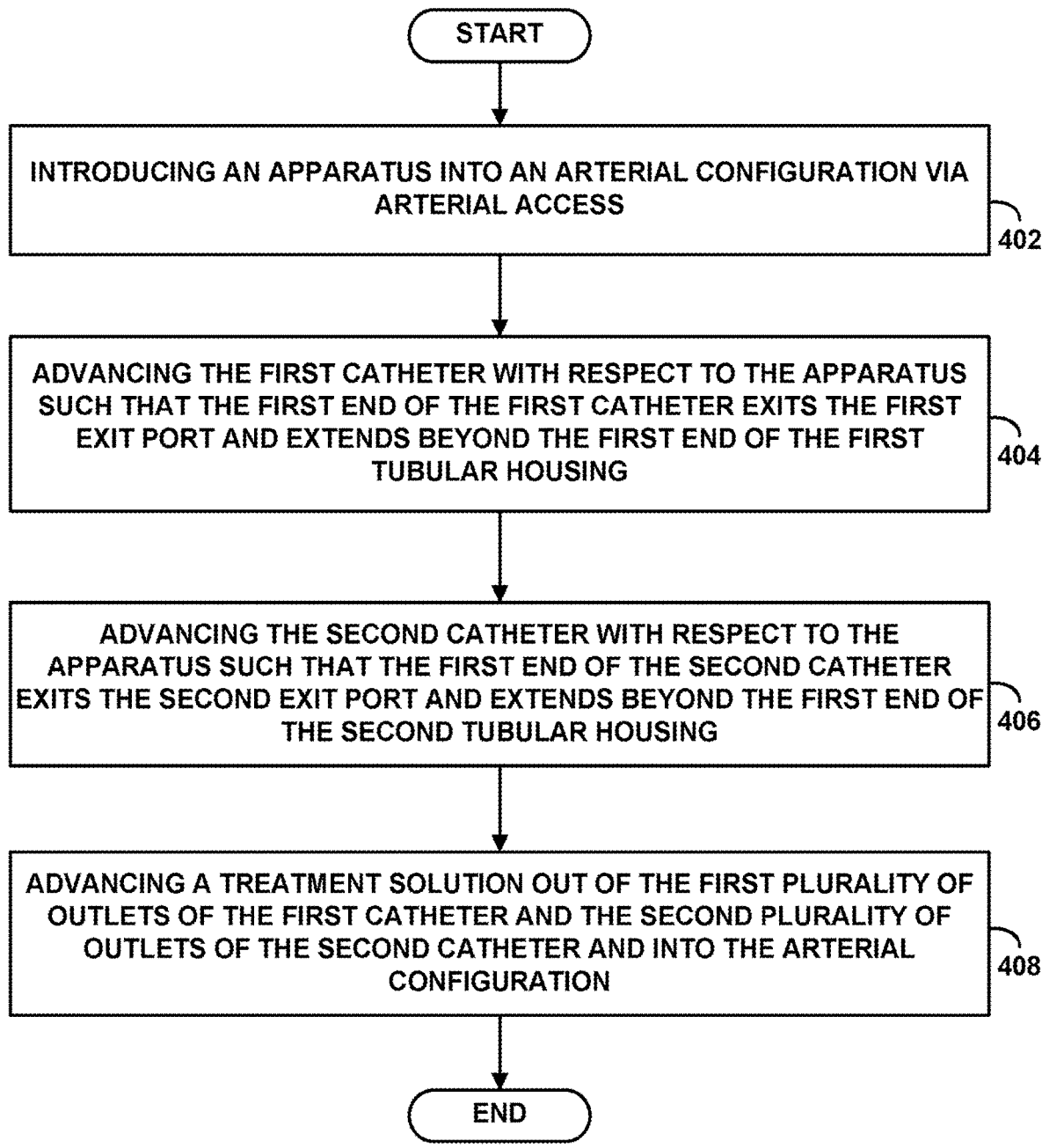
FIG. 8 is a flow chart depicting functions that can be carried out in accordance with example embodiments of the disclosed methods.

FIG. 8 is a simplified flow chart illustrating a method according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 402, the method 400 includes introducing the apparatus 100 of any of the embodiments described above in relation to FIGS. 1-7 into an arterial configuration via arterial access. At block 404, the method includes advancing the first catheter 132 with respect to the first tubular housing 102 such that the first end 134 of the first catheter 132 exits the first exit port 110 and extends beyond the first end 106 of the first tubular housing 102. At block 406, the method includes advancing the second catheter 140 with respect to the second tubular housing 112 such that the first end 142 of the second catheter 140 exits the second exit port 120 and extends beyond the first end 116 of the second tubular housing 112. At block 408, the method includes advancing a treatment solution out of the first plurality of outlets 138 of the first catheter 132 and the second plurality of outlets 146 of the second catheter 140 and into the arterial configuration.

In one example, the treatment solution may be advanced through the first catheter 132 and the second catheter 140 at a flow rate in the range of about 5 cc/hr to about 100 cc/hr.

In one embodiment, the method may further include monitoring a blood pressure, via the pressure transducer 150, after introducing the apparatus 100 within the arterial configuration. This may permit a user to establish a patient's base line blood pressure. In a catheter-directed lytic infusion to the pulmonary arteries, the apparatus 100 may be left in place for 12-36 hours. If the patient is under monitoring by an ICU nurse, the nurse can monitor the blood pressure or the system can have an alarm or infusion control stop when the pulmonary artery pressure reaches a pre-prescribed level. Then, the method involves monitoring the blood pressure, via the pressure transducer 150, after advancing the treatment solution to the first plurality of outlets 138 of the first catheter 132 and the second plurality of outlets 146 of the second catheter 140. This may permit a user to determine when the treatment solution has reduced or removed a blockage by observing a decrease in blood pressure. In one embodiment, the blood pressure that is monitored may be a pulmonary artery pressure, for example.

In another example, the method may further include the steps of inflating a balloon 158 coupled to the first end 134 of the first catheter 132, and advancing the first end 134 of the first catheter 132, via the balloon 158, to the arterial configuration. In this embodiment, the inflated balloon 158 may be acted upon by blood flow. In another example, the method may further include the steps of inflating a balloon coupled to the first end 106 of the first tubular housing 102, and advancing the first end 106 of the first tubular housing 102, via the balloon, to the arterial configuration. In another example, the method may further include introducing a guidewire into the arterial configuration via arterial access, and advancing the apparatus 100 along the guidewire to the arterial configuration.

In another example, the arterial configuration is the pulmonary artery, and the method further includes the steps of positioning the first end 134 of the first catheter 132 into a first branch 212 of the pulmonary artery 206, and positioning the first end 142 of the second catheter 140 into a second branch 214 of the pulmonary artery 206.

The method may further include determining a first blood pressure, via the pressure transducer 150 at a first time, determining a second blood pressure, via the pressure transducer 150 at a second time, and comparing the first blood pressure to the second blood pressure to determine a change in blood pressure. This may permit a user to determine when the treatment solution has reduced or removed a blockage by observing a decrease in pulmonary artery blood pressure over time.

In another embodiment, the method further includes determining, via the pressure transducer 150, a blood pressure is less than a threshold value, and responsively removing the apparatus 100 from the arterial configuration. The pulmonary artery pressure for an unblocked artery may range from about 20 mmHg to about 35 mmHg though such a range may vary with age, fluid status and other underlying medical conditions. As such, the threshold value may be in the range from about 20 mmHg to about 35 mmHg.

In another embodiment, the method may include subcutaneously implanting a pump 188, where the pump 188 is coupled to the first catheter 132 and the second catheter 140. In such an embodiment, the pump 188 may be configured to be implanted into one of a buttock, a thigh, or an abdomen.

In yet another embodiment, the method further includes the steps of determining, via the pressure transducer 150, that a blood pressure is greater than a threshold value, and in response to the determination that the blood pressure is greater than the threshold value, activating a pump 188 to advance the treatment solution out of the first plurality of outlets 138 of the first catheter 132 and the second plurality of outlets 146 of the second catheter 140. Such a method may further include the steps of determining, via the pressure transducer 150, that a blood pressure is less than a threshold value, and in response to the determination that the blood pressure is less than the threshold value, deactivating the pump 188. Such a method may be used to treat pulmonary hypertension or heart failure of a patient.

In the above description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts were described in conjunction with specific examples, it will be understood that these examples are not intended to be limiting.

The invention claimed is:

1. An apparatus comprising:
   a first tubular housing defining a first lumen, the first tubular housing having a first end and a second end, wherein the first end of the first tubular housing includes a first exit port;
   a second tubular housing defining a second lumen, the second tubular housing having a first end and a second end, wherein the first end of the second tubular housing includes a second exit port;
   a third tubular housing defining a third lumen, the third tubular housing having a first end and a second end, wherein the third tubular housing is coupled to at least one of the first tubular housing and the second tubular housing such that each of the first tubular housing, the second tubular housing, and the third tubular housing are fixed with respect to one another;
   a first catheter having a first end and a second end, wherein a portion of the first catheter arranged near the first end of the first catheter includes a first plurality of outlets, wherein the first catheter is configured to be positioned at least partially within the first tubular housing, wherein a shape of the first catheter is complementary to a shape of the first tubular housing such that the first catheter cannot rotate with respect to the first tubular housing as the first catheter moves longitudinally with respect to the first tubular housing;
   a second catheter having a first end and a second end, wherein a portion of the second catheter near the first end of the second catheter includes a second plurality of outlets, and wherein the second catheter is configured to be positioned at least partially within the second tubular housing;
   a pressure transducer line positioned in the third lumen of the third tubular housing; and
   a pressure transducer coupled to the pressure transducer line.

2. The apparatus of claim 1, wherein the first end of each of the first catheter and the second catheter comprises a curved section.

3. The apparatus of claim 2, wherein the curved sections of each of the first catheter and the second catheter have a radius in a range from about 3 cm to about 500 cm.

4. The apparatus of claim 1, wherein the first catheter is configured to move longitudinally within the first tubular housing for a fixed distance.

5. The apparatus of claim 4, wherein the fixed distance ranges from about 0 cm to about 100 cm.

6. The apparatus of claim 1, further comprising:
   a balloon coupled to the first end of the first catheter.

7. The apparatus of claim 1, further comprising:
   a sheath having a first end and a second end, wherein the sheath is positioned around each of the first tubular housing, the second tubular housing, and the third tubular housing; and
   a balloon coupled to the first end of the sheath.

8. The apparatus of claim 1, further comprising:
   a balloon coupled to one of the first end of the first tubular housing, the first end of the second tubular housing, or the first end of the third tubular housing.

9. The apparatus of claim 1, wherein the first end of the first catheter and/or the first end of the second catheter comprises one of an angled pigtail shape, a shepherd's hook shape, or an angled hook shape.

10. The apparatus of claim 1, wherein the first catheter and the second catheter are independently moveable between a pre-deployment position and a deployed position, wherein the first end of the first catheter is positioned substantially within the first tubular housing when the first catheter is in the pre-deployment position, wherein the first end of the second catheter is positioned substantially within the second tubular housing when the second catheter is in the pre-deployment position, wherein the first end of the first catheter is configured to extend out of the first exit port when the first catheter is in the deployed position, and wherein the first end of the second catheter is configured to extend out of the second exit port when the second catheter is in the deployed position.

11. The apparatus of claim 10, further comprising:
a first catheter diverter configured to at least partially obstruct the first lumen of the first tubular housing, such that the first catheter contacts the first catheter diverter and is thereby directed at an angle through the first exit port of the first tubular housing when transitioning from the pre-deployment position to the deployed position; and
a second catheter diverter configured to at least partially obstruct the second lumen of the second tubular housing, such that the second catheter contacts the second catheter diverter and is thereby directed at an angle through the second exit port of the second tubular housing when transitioning from the pre-deployment position to the deployed position.

12. The apparatus of claim 11, wherein the first catheter diverter comprises a first angled tab extending from the first end of the first tubular housing at an angle with respect to a longitudinal axis of the first tubular housing, and wherein the second catheter diverter comprises a second angled tab extending from the first end of the second tubular housing at an angle with respect to a longitudinal axis of the second tubular housing.

13. The apparatus of claim 12, wherein the first angled tab and the second angled tab are flexible.

14. The apparatus of claim 1, wherein the pressure transducer line is moveable with respect to the third tubular housing.

15. The apparatus of claim 1, wherein the first plurality of outlets defined along the portion of the first catheter arranged near the first end of the first catheter and the second plurality of outlets defined along the portion of the second catheter arranged near the first end of the second catheter are positioned in a helical pattern.

16. The apparatus of claim 1, wherein the first catheter and the second catheter have an inner diameter in a range of about 1.5 French to about 15 French.

17. The apparatus of claim 1, wherein the first plurality of outlets defined along the portion of the first catheter arranged near the first end of the first catheter extend along a length ranging from about 3 cm to about 40 cm, and wherein the second plurality of outlets defined along the portion of the second catheter arranged near the first end of the second catheter extend along a length ranging from about 3 cm to about 40 cm.

18. The apparatus of claim 1, further comprising:
a first hemostatic valve disposed within the portion of the first catheter arranged near the first end of the first catheter; and
a second hemostatic valve disposed within the portion of the second catheter arranged near the first end of the second catheter.

19. The apparatus of claim 1, wherein the first exit port and the second exit port are angled away from each other so as to direct the first catheter and the second catheter in relative opposite directions.

20. The apparatus of claim 19, wherein a longitudinal axis extending through a center of the first exit port is arranged at an angle relative to a longitudinal axis extending through a center of the second exit port, and wherein the angle ranges from about 15 degrees to about 180 degrees.

21. The apparatus of claim 1, wherein a shape of the second catheter is complementary to a shape of the second tubular housing such that the second catheter cannot rotate with respect to the second tubular housing as the second catheter moves longitudinally with respect to the second tubular housing.

22. The apparatus of claim 1, further comprising:
a first rail positioned in the first lumen of the first tubular housing, wherein the first rail is configured to mate with a corresponding rail positioned on an external surface of the first catheter; and
a second rail positioned in the second lumen of the second tubular housing, wherein the second rail is configured to mate with a corresponding rail positioned on an external surface of the second catheter.

23. The apparatus of claim 1, further comprising:
a first pump coupled to at least one of the first catheter and the second catheter; and
a reservoir coupled to the first pump.

24. The apparatus of claim 23, further comprising:
a sensor positioned in the reservoir, wherein the sensor is configured to determine a volume of treatment solution remaining in the reservoir; and
a wireless communication interface in communication with the sensor, the wireless communication interface configured to transmit the determined volume to a computing device.

25. The apparatus of claim 23, further comprising:
a housing positioned around the first pump and the reservoir, wherein the housing includes a biocompatible outer surface.

26. The apparatus of claim 23, further comprising:
a controller coupled to the first pump, wherein the controller is configured to:
determine, via the pressure transducer, that a blood pressure is greater than a threshold value; and
in response to the determination that the blood pressure is greater than the threshold value, activate the first pump to advance a treatment solution out of the first plurality of outlets of the first catheter and the second plurality of outlets of the second catheter.

27. The apparatus of claim 26, wherein the controller is further configured to:
determine, via the pressure transducer, a blood pressure is less than the threshold value; and
in response to the determination that the blood pressure is less than the threshold value, deactivate the first pump.

28. The apparatus of claim 26, wherein the controller is further configured to:
determine that one or more of an oxygen saturation or a heart rate is greater than a threshold value; and
in response to the determination that either the oxygen saturation or the heart rate is greater than the threshold value, activate the first pump to advance a treatment solution out the first plurality of outlets of the first catheter and the second plurality of outlets of the second catheter.

29. The apparatus of claim 28, wherein the controller is further configured to:
determine an oxygen saturation or a heart rate; and
in response to the determination that either the oxygen saturation is below a threshold value or the heart rate is above a threshold value, deactivate the first pump.

30. A method comprising:
introducing the apparatus of claim 1 into an arterial configuration via arterial access;
advancing the first catheter with respect to the first tubular housing such that the first end of the first catheter exits the first exit port and extends beyond the first end of the first tubular housing;

advancing the second catheter with respect to the second tubular housing such that the first end of the second catheter exits the second exit port and extends beyond the first end of the second tubular housing; and advancing a treatment solution out of the first plurality of outlets of the first catheter and the second plurality of outlets of the second catheter and into the arterial configuration.

31. An apparatus comprising:
a first tubular housing defining a first lumen, the first tubular housing having a first end and a second end, wherein the first end of the first tubular housing includes a first exit port;
a second tubular housing defining a second lumen, the second tubular housing having a first end and a second end, wherein the first end of the second tubular housing includes a second exit port;
a third tubular housing defining a third lumen, the third tubular housing having a first end and a second end, wherein the third tubular housing is coupled to at least one of the first tubular housing and the second tubular housing such that each of the first tubular housing, the second tubular housing, and the third tubular housing are fixed with respect to one another;
a first catheter having a first end and a second end, wherein a portion of the first catheter arranged near the first end of the first catheter includes a first plurality of outlets, and wherein the first catheter is configured to be positioned at least partially within the first tubular housing;
a second catheter having a first end and a second end, wherein a portion of the second catheter near the first end of the second catheter includes a second plurality of outlets, and wherein the second catheter is configured to be positioned at least partially within the second tubular housing;
a first flow control device arranged near the first end of the first catheter, wherein the first flow control device allows a treatment solution to pass through the first plurality of outlets but minimizes back flow of blood into the first catheter;
a second flow control device arranged near the first end of the second catheter, wherein the second flow control device allows a treatment solution to pass through the second plurality of outlets but minimizes back flow of blood into the second catheter;
a pressure transducer line positioned in the third lumen of the third tubular housing; and
a pressure transducer coupled to the pressure transducer line.

* * * * *